United States Patent [19]

Kanno et al.

[11] Patent Number: 4,619,739
[45] Date of Patent: Oct. 28, 1986

[54] METHOD AND APPARATUS FOR MEASURING HALOGEN ION CONCENTRATION

[75] Inventors: Ken-ichi Kanno; Tetsuya Gatayama; Masao Koyama; Junji Koezuka, all of Yokohama, Japan

[73] Assignee: Kabushiki Kaisha Toshiba, Kawasaki, Japan

[21] Appl. No.: 815,467

[22] Filed: Jan. 2, 1986

[30] Foreign Application Priority Data

Jan. 14, 1985 [JP] Japan .................................. 60-4361
Jan. 14, 1985 [JP] Japan .................................. 60-4362

[51] Int. Cl.$^4$ ...................... G01N 27/28; G01N 27/50
[52] U.S. Cl. ..................................... 204/1 T; 204/401; 204/402; 204/409; 204/416; 422/68; 436/125
[58] Field of Search ............... 436/124, 125, 150, 166; 422/68, 81; 204/1 T, 1 B, 401, 402, 409, 416

[56] References Cited

FOREIGN PATENT DOCUMENTS 22433 7/1975 Japan .................................. 204/1 B
658459 4/1979 U.S.S.R. ............................. 204/1 B

*Primary Examiner*—G. L. Kaplan
*Attorney, Agent, or Firm*—Oblon, Fisher, Spivak, McClelland & Maier

[57] ABSTRACT

A halogen ion concentration in a solution is measured by bringing halogen ion-selective detection means comprising a silver/silver halide electrode, and a reference electrode into a solution whose halogen ion concentration is to be measured, and measuring an electromotive force of the halogen ion-selective detection means in the presence of silver ions dissolved in the solution. The electromotive force corresponds to the halogen ion concentration in the solution.

15 Claims, 9 Drawing Figures

F I G. 6
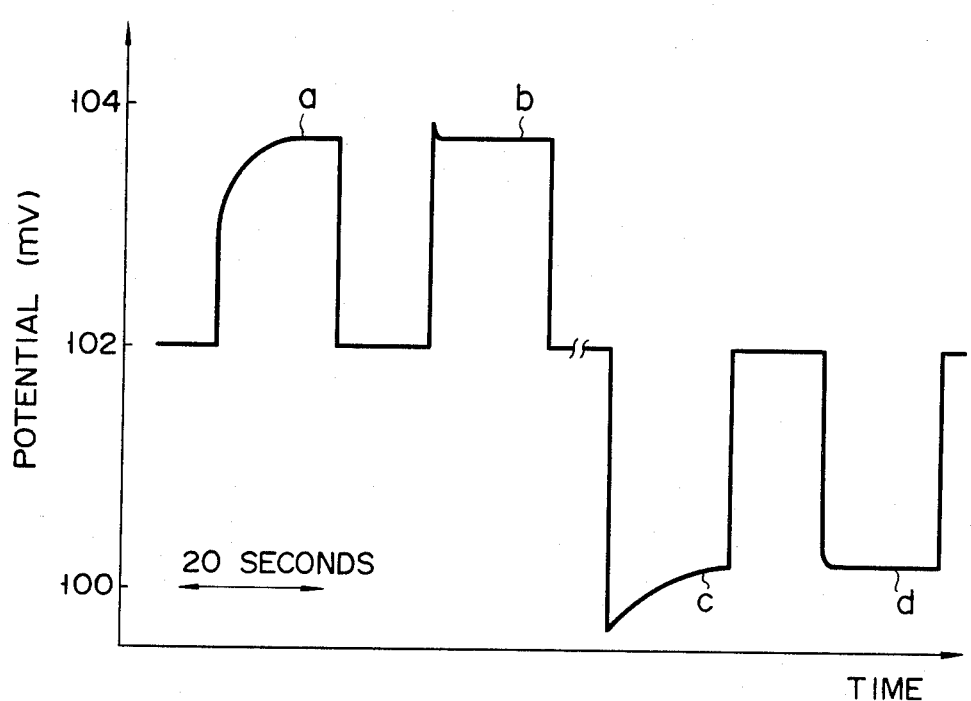

METHOD AND APPARATUS FOR MEASURING HALOGEN ION CONCENTRATION

BACKGROUND OF THE INVENTION

1. Field of the Invention

The present invention relates to a method and apparatus for measuring a halogen ion concentration and, more particularly, to a method and apparatus for measuring a halogen ion concentration using a halogen ion-selective electrode.

2. Description of the Prior Art

An ion-selective electrode has a linear relationship between its electromotive force E and a logarithm for concentration of specific ions in a solution. Thus, when an electromotive force of a solution, which contains specific ions at an unknown concentration, is measured, the concentration of the specific ions can be determined. In recent years, such as ion-selective electrode has been used in medical quantitative analysis of ions (e.g., sodium ions, potassium ions, chloride ions, and the like, particularly those contained in blood).

For chloride ion-selective electrodes, an electrode having on its surface a polyvinyl chloride film, in which chloride ion-selective material comprising a quanternary ammonium salt is dispersed, and an electrode having on its surface an ion-selective solid film, which is formed by compression molding a silver sulfide and silver chloride compound, have been developed and widely used in biochemical analyzers.

However, an organic material such as protein becomes easily attached to electrodes of the former constructions, or the electrodes are easily interfered with by other negative ions. Attachment of protein on such electrodes causes a serious problem: When serum protein becomes attached to an electrode surface during serum analysis, the sensitivity of the electrode is degraded, and response time is considerably delayed, thus shortening the electrode's working life.

In an electrode of the second construction, a mixing ratio of $Ag_2S$ and $AgCl$ must be accurately determined, and the electrode must be compression molded under high pressure, therefore, it is difficult to form a compact electrode, or an electrode in a desired shape, resulting in limited manufacture thereof. Furthermore, in order to simultaneously analyze several types of electrolytes in blood, a flow-through type ion sensor which integrates a chlorine ion-selective electrode, another ion-selective electrode, and an ion concentration measurement cell is preferably used. Particularly in the latter electrode, since it is difficult to mold it into a desired shape, such an electrode cannot be installed in the flow-through type ion sensor.

On the contrary, a silver/silver halide electrode (e.g., a silver/silver chloride electrode) is relatively free from the above problems, and has been receiving a great deal of attention for medical applications. However, in general, dissolution of silver ions from the silver/silver halide electrode proceeds until a saturated silver halide layer is formed around the electrode, and thus the electrode potential deviates correspondingly. As a result, the silver/silver halide electrode exhibits poor responsivity to halogen ions to be measured, namely exhibits delayed response time. This problem becomes particularly significant in a biochemical analysis wherein very small changes of halogen ion concentrations must be detected accurately. For example, blood serum usually contains chloride ions at a concentration of about 110 mEq. The concentration mentioned generally deviates within a range of +10 mEq in a normal serum. This deviation corresponds to electrode potential change of only ±2–±3 mV. Potential change until a saturated silver chloride is formed around the electrode by elution of silver ions from the electrode is too large to be neglected against the above-noted potential change corresponding to the changes of the halogen ion concentration, and causes the delayed response.

SUMMARY OF THE INVENTION

It is therefore an object of the present invention to provide a method and apparatus for measuring a halogen ion concentration in a solution, more specifically, blood serum, using a silver/silver halide electrode with short response time.

According to one aspect of the present invention, there is provided a method for measuring a halogen ion concentration in a solution, comprising the steps of:

bringing halogen ion detection means comprising a silver/silver halide electrode, and a reference electrode into a solution whose halogen ion concentration is to be measured; and measuring an electromotive force of the halogen ion detection means corresponding to the halogen ion concentration of the solution in the presence of silver ions dissolved in the solution.

According to another aspect of the present invention there is provided an apparatus for measuring a halogen ion concentration in a solution, comprising:

an ion-selective electrode unit including a halogen ion-selective electrode comprising a silver/silver halide electrode;

a cell, having a flow path for the solution, for supporting said ion-selective electrode unit so as to expose it into said flow path;

means for introducing the solution into said flow path of said cell;

means for dissolving silver ions in the solution;

potential measurement means for measuring a potential of said ion-selective electrode unit when the solution in which the silver ions are dissolved is introduced into said flow path; and means for calculating an ion concentration in the solution based on the potential measured by said potential measurement means.

BRIEF DESCRIPTION OF THE DRAWINGS

FIG. 6 is a graph showing response time of the silver/silver halide electrode when a chloride ion concentration is measured in accordance with the method of the present invention, together with a comparison.

DETAILED DESCRIPTION OF THE PREFERRED EMBODIMENTS

Figure 1:
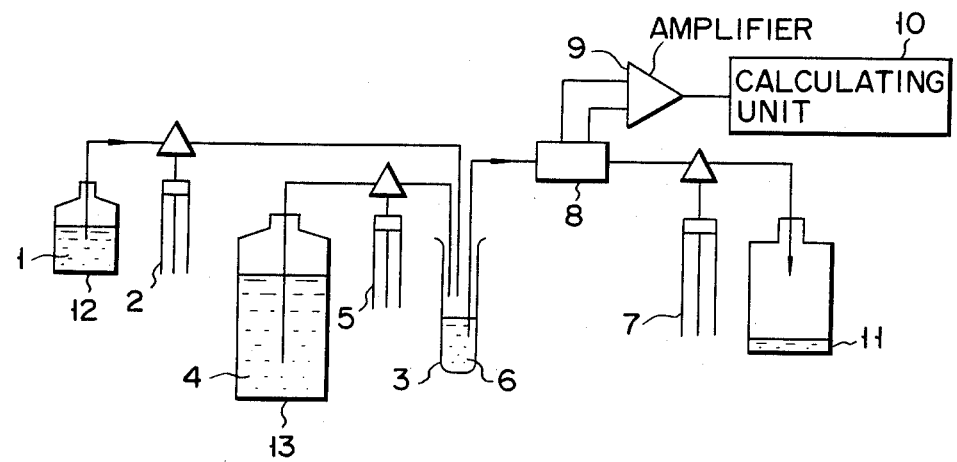
FIG. 1 is a schematic view of a halogen ion concentration measurement apparatus according to a first embodiment of the present invention.

The present invention have made extensive studies on improving the response time of a silver/silver halide electrode without impairing its inherent advantages. It was found from these studies that, in order to achieve the object of the present invention, silver ions must be dissolved in a solution whose halogen ion concentration is to be measured.

Electrodes used as a halogen ion-selective electrode in the present invention include, as silver/silver halide electrodes, a silver/silver chloride electrode, a silver/silver bromide electrode, and a silver/silver iodide electrode. These silver/silver halide electrodes are known to those skilled in the art, and each has a silver halide layer formed on a silver substrate (e.g., a silver wire). These electrodes exhibit individual halogen ion selectivity depending on the type of silver halide layer. For example, when a silver halide layer comprises silver chloride, the silver/silver halide electrode generates an electromotive force selectively corresponding to the chloride ion concentration in a solution.

In order to measure a halogen ion concentration in a solution according to the method of the present invention, a halogen ion-selective detection means, comprising a silver/silver halide electrode, is dipped in a solution (more specifically, an aqueous solution such as blood serum) together with a reference electrode (e.g., a saturated calomel electrode). An electromotive force (corresponding to a halogen ion concentration in the solution) of the silver/silver halide electrode against the reference electrode is then measured. In the method of the present invention, silver ions are dissolved in the solution.

Silver ions can be supplied into the solution through a water soluble silver compound. Such a compound includes a silver halide (e.g., silver chloride, silver bromide), silver nitrate and so on.

In order to dissolve silver ions in the solution to be measured, a silver compound is directly added to the solution or is dissolved in advance in a diluent solution to be added to the sample solution (serum), after which it is subjected to ion concentration measurement. Alternatively, an inner wall of a flow path through which the sample solution flows is formed of the above-mentioned silver compound, and when the sample solution is in contact with the wall, silver ions can be dissolved thereinto.

A silver ion concentration in a solution to be measured is at least 10% of the saturate concentration of silver ions in the solution. The silver ion concentration is preferably 50% or more of the saturated concentration and most preferably is the saturated concentration.

After the electromotive force of the silver/silver halide electrode against the reference electrode in a sample solution is measured, a halogen ion concentration in the corresponding solution can be determined based on a calibration curve, which is prepared in advance and shows the relationship between the electromotive force and halogen ions.

Silver ions can be used even if they are not dissolved in a sample solution. Usually, every time a halogen ion measurement operation is completed, a silver/silver halide electrode is washed in a washing solution, and after a predetermined number of measurement operations are completed, sensitivity of the silver/silver halide electrode is measured in a calibration solution, and a calibration curve is reformed. It was found by the present inventors that when silver ions are dissolved in a washing or calibration solution used as above, degradation in sensitivity of a silver/silver halide electrode can be prevented, and life time of the electrode can be prolonged. In addition, when silver ions are dissolved in a stocking solution for silver/silver halide electrodes, the same effects can be obtained.

When silver halide corresponding to a type of halogen ion to be measured is used as the silver ion supply source, dissolution of the silver halide layer of a silver/silver halide electrode can be suppressed. For example, in order to measure a chloride ion concentration, when silver chloride is dissolved in the sample solution and in the washing, calibration, and stocking solutions and the like, dissolution of the silver chloride layer of a silver/silver chloride electrode used can be prevented.

The present inventors found that, in addition to silver ions, a pH concentration of diluent, washing, calibration, and/or stocking solutions (to be referred to as standard solutions hereinafter), is preferably in a range of 6.8 to 7.6, so that life time of a silver/silver halide electrode can be prolonged. These standard solutions preferably comprise an aqueous solution (tris-borate buffer solution) containing tris(hydroxymethyl)amino methane and boric acid.

An apparatus for carrying out the method of the present invention will be described with reference to the accompanying drawings.

FIG. 1 shows a first embodiment of an ion concentration analysis apparatus used in the method of the present invention. A predetermined amount (e.g., 40 $\mu$l) of serum 1 in container 12 is supplied to sample tube 3 by serum suction pump 2. A predetermined amount (e.g., 360 $\mu$l) of diluent solution 4 in container 13 is also supplied to sample tube 3, by diluent solution suction pump 5. Diluent solution 4 comprises ion-exchange water in which, e.g., AgCl is dissolved in its saturate concentration of $2.5 \times 10^{-5}$ mol/l. In sample tube 3, serum 1 and diluent solution 4 are stirred, and prepared solution 6, in which components of serum 1 are diluted to 1/10, is prepared. Prepared solution 6 is supplied to flow-through type ion sensor 8, which comprises a silver/silver chloride electrode (as a $Cl^-$ ion-selective electrode), an $Na^+$ ion-selective electrode, a $K^+$ ion-selective electrode, a reference electrode and a measurement cell. The potential difference between individual ion-selective electrodes and the reference electrode is amplified by amplifier 9, and the amplified electrical signals are supplied to calculating unit 10, thus performing given ion concentration measurement. After such measurement, prepared solution 6 is transferred to discharge liquid tank 11.

After the above-mentioned ion concentration measurement of serum 1 is completed, in order to perform the next serum measurement, only diluent solution 4 is injected into sample tube 3, thereby washing it. Calibration solutions of predetermined high and low chloride ion concentrations are sequentially supplied from a container (not shown) to ion sensor 8, so as to calibrate electrode sensitivity. In addition, a measured potential is calibrated using a calibration solution of an ion concentration approximate to the measured concentration. AgCl is also dissolved in this calibration solution.

Ion sensor 8, having a structure such as those shown in FIG. 4 or 5, will be described more specifically hereinafter.

Figure 4:
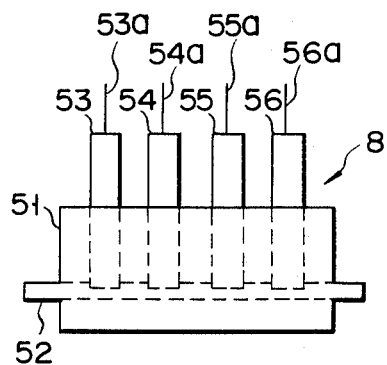
FIG. 4 is a schematic sectional view of a flow-through type ion sensor used in the apparatus of the present invention.

In flow-through type ion sensor 8 shown in FIG. 4, flow path 52 for a measured solution extends through the interior of measurement cell body 51, with $Na^+$ ion-selective electrode 53, $K^+$ ion-selective electrode 54, silver/silver chloride electrode 55 (as a $Cl^-$ ion-selective electrode), and reference electrode 56 supported thereon. One end portion of electrodes 53, 54, and 55 at which ion-sensitive portions are formed, and one end portion of electrode 56 at which a liquid-junction portion is formed are inserted in path 52, with lead wires 53a to 56a connected to the other end portions of respective electrodes.

Figure 5:
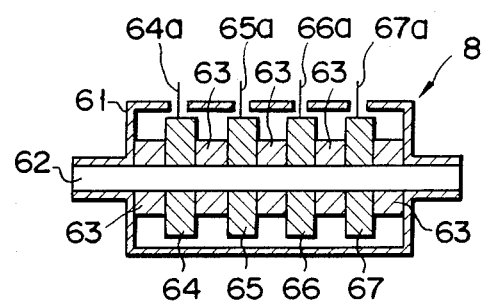
FIG. 5 is a schematic sectional view of another flow-through type ion sensor used in the apparatus of the present invention.

In flow-through type ion sensor 8 shown in FIG. 5, flow holes 62 for a sample solution are formed in two end faces of cylindrical measurement cell body 61, with ring-shaped $Na^+$ ion-selective electrode 64, $K^+$ ion-selective electrode 65, silver/silver chloride electrode 66 (as a $Cl^-$ ion-selective electrode), and reference electrode 67 housed in cell body 61 so as to interpose spacer 63, having a flow hole corresponding to hole 62 at its center, between each two adjacent electrodes. Lead wires 64a to 67a are connected to portions of these electrodes, and are extended outside cell body 61. Note that each ion-selective electrode has an ion sensitive portion near flow hole 62, as is a liquid-junction portion of reference electrode 67.

Figure 2:
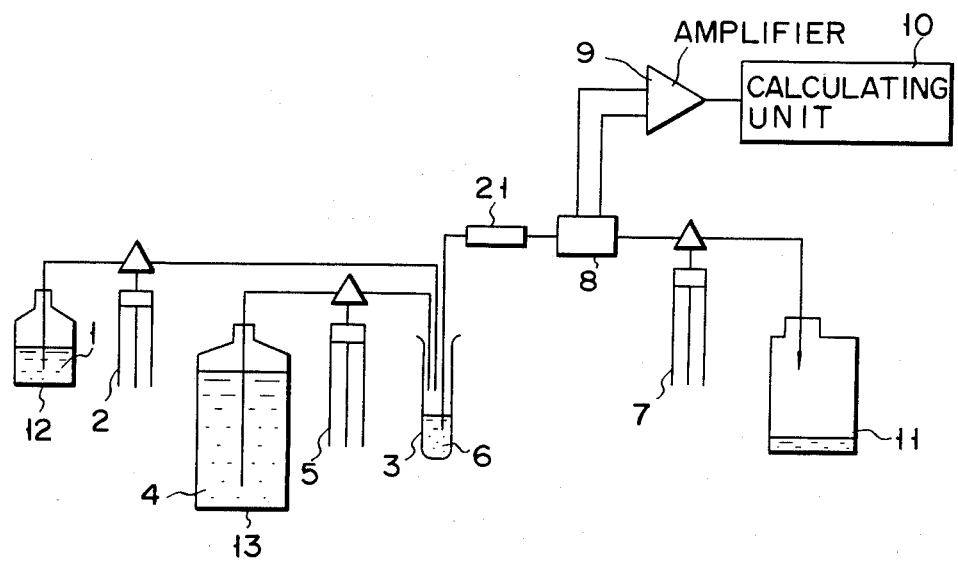
FIG. 2 is a schematic view showing a halogen ion concentration measurement apparatus according to a second embodiment of the present invention.

FIG. 2 shows another embodiment of an ion concentration measurement apparatus, comprising another means for using a silver halide (e.g., silver chloride) as a silver ion supply source. The same reference numerals in FIG. 2 denote the same parts as in FIG. 1, and a detailed description thereof will be omitted.

In the apparatus of FIG. 2, diluent solution 4 does not contain silver ions, and comprises only a tris-borate buffer solution. In this apparatus, AgCl pipe 21 is provided midway along a liquid supply pipe for supplying solution 6 in sample tube 3 to flow-through type ion sensor 8. AgCl pipe 21 is formed in such a manner that a through hole, having the same 1.5 mm diameter as that of the liquid supply pipe, is formed in an Ag bar having an outer diameter of 4 mm and a length of 30 mm. The resulting pipe is then electrolyzed, so that an AgCl layer is formed on the inner wall of the through hole. An amount of serum used can be 50 μl, and that of a diluent solution can be 450 μl.

A measuring method using the ion concentration measurement apparatus of this embodiment is the same as that of the apparatus shown in FIG. 1, obtaining the same results and advantages. In this case, however, AgCl is dissolved in solution 6 from AgCl pipe 21.

Figure 3:
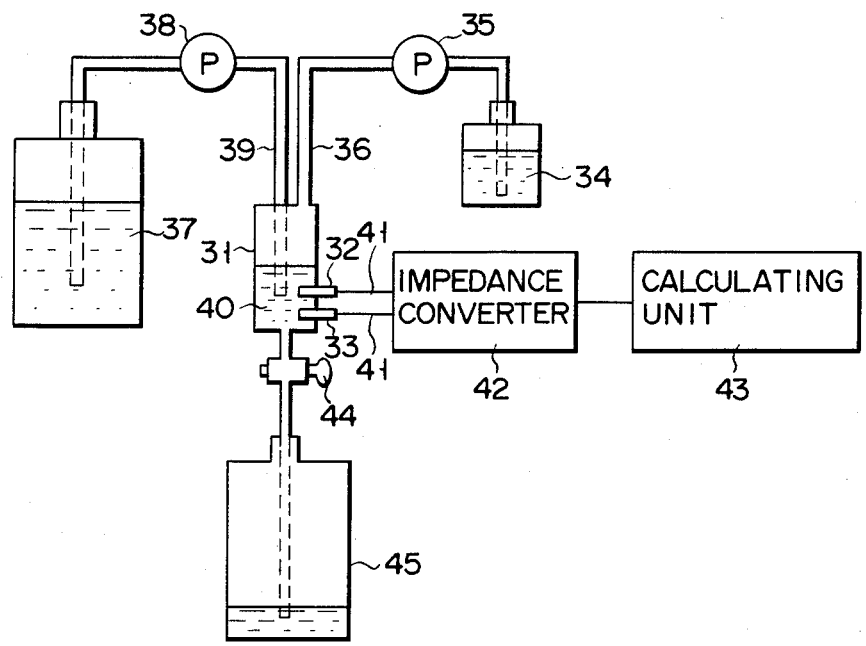
FIG. 3 is a schematic view showing a halogen ion concentration measurement apparatus according to a third embodiment of the present invention.

FIG. 3 shows another chloride ion concentration analysis apparatus used in the method of the present invention.

Referring to FIG. 3, $Cl^-$ ion-selective electrode 32 and reference electrode 33 are inserted near a bottom portion of measurement cell 31. Serum 34 is supplied into measurement cell 31 through pipe 36 by pump 35. Diluent solution (also acting as a washing solution) 37 is supplied into cell 31 through pipe 39 by pump 38. $Ag^+$ ions are dissolved in solution 37 by adding, e.g., AgCl. Serum 34 and solution 37 are stirred in cell 31, thus preparing measured solution 40, in which serum is diluted to a predetermined concentration. Electrical signals obtained by electrodes 32 and 33 are supplied to impedance converter 42 and calculating unit 43 through lead wires 41, thus enabling $Cl^-$ ion concentration measurement. After measurement is completed, solution 40 is supplied to discharge liquid container 45 by opening cock 44. Thereafter, only solution 37 is supplied into cell 31, thus washing it.

TEST EXAMPLE 1

Control serum containing chloride ions at a concentration of 92 mM were diluted with a tris-borate buffer solution (pH 7.4), thus preparing a test solution. A silver/silver halide electrode was dipped in the prepared solution together with a reference electrode, and potential of the silver/silver halide electrode was measured. In this example, measurement was performed when 10 ppm of silver ions were added to the test solution (as per the present invention), and when no silver ions were added. FIG. 6 shows the test results. In FIG. 6, curve a indicates the case wherein no silver ions are added, and curve b indicates the case wherein silver ions are added.

TEST EXAMPLE 2

The same test as above was conducted, except that the serum contained 108 mM of chloride ions. FIG. 6 also shows the test results. In FIG. 6, curve c indicates the case wherein no silver ions were added, and curve d indicates the case wherein silver ions were added.

As can be seen from FIG. 6, when silver ions are dissolved in a test solution in accordance with the method of the present invention, response time is considerably improved.

TEST EXAMPLE 3

Figure 7:
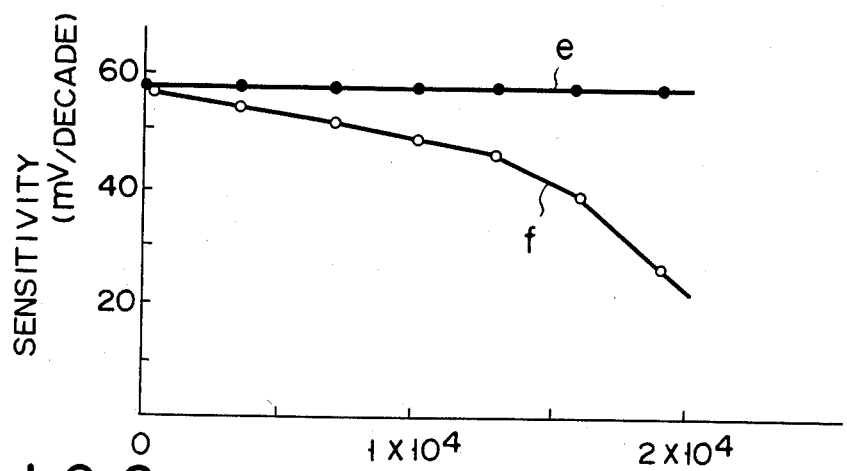
FIGS. 7 to 9 are graphs showing a change in sensitivity of the silver/silver halide electrode over time when a chloride concentration is measured in accordance with the method of the present invention, together with a comparison.

In this test, a change in sensitivity of a silver/silver chloride electrode over time was measured when a chloride ion concentration in serum was continuously measured using the apparatus of FIG. 1. For a diluent solution, ion-exchange water containing silver chloride at a saturate concentration (as per the present invention), and water containing no silver ions were used. 40 μl of serum and 360 μl of a diluent solution were used for each sample. FIG. 7 shows the test results. In FIG. 7, curve e indicates the case wherein deionized water in which silver chloride was dissolved was used, and curve f indicates the case wherein only deionized water was used.

TEST EXAMPLE 4

Figure 8:
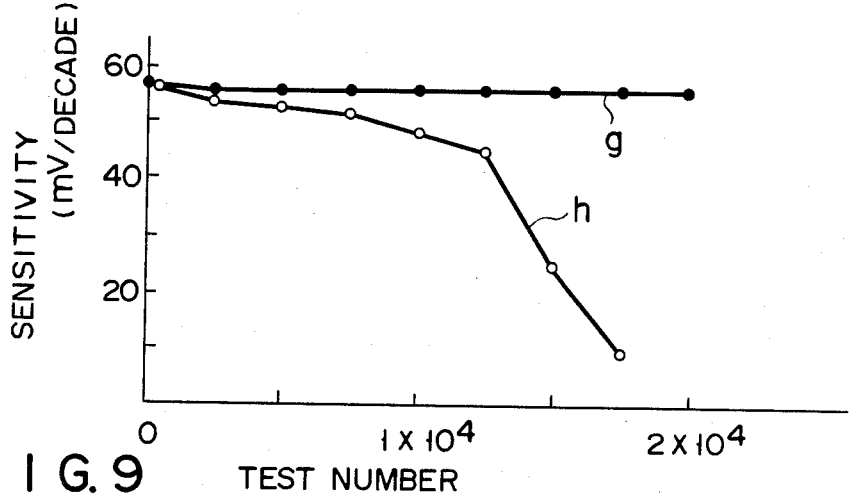

In this test, a change in sensitivity of a silver/silver chloride electrode over time was measured when a chloride ion concentration in serum was continuously measured using the apparatus of FIG. 1. For a diluent solution, tris-borate buffer solutions (pH 7.4) that contained 1 ppm of silver nitrate and did not contain the nitrate at all were used. 50 μl of serum and 450 μl of the diluent solution were used for each sample. Thus, in the sample containing silver ions, the silver ions are present at the saturated concentration. FIG. 8 shows the test results. In FIG. 8, curve g indicates the case wherein the buffer solution added with silver nitrate was used, and curve h indicates the case wherein the buffer solution without addition of silver nitrate was used.

As can be seen from FIGS. 7 and 8, according to the present invention, sensitivity of a silver/silver chloride electrode was not degraded over a long period of time.

TEST EXAMPLE 5

Figure 9:
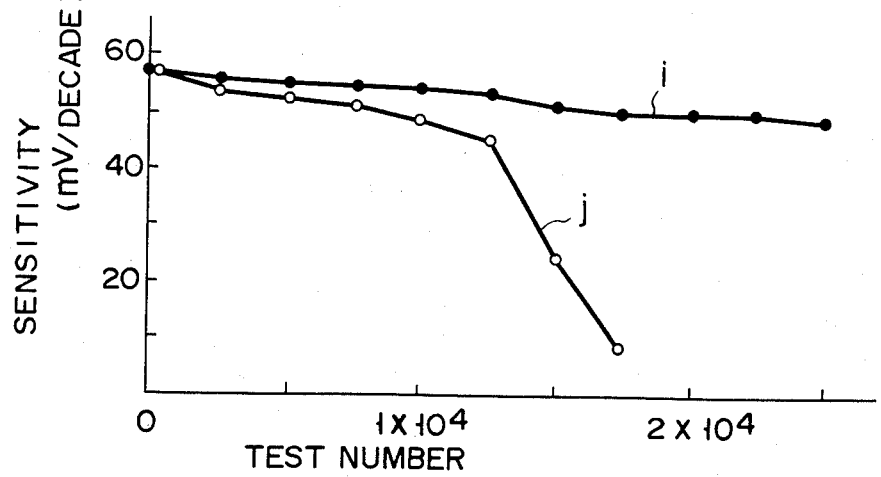

In this test, a change in sensitivity of a silver/silver chloride electrode over time was measured when a chloride ion concentration in serum was continously measured using the apparatus of FIG. 2. For a diluent solution, a tris-borate buffer solution (pH 7.4) was used. 50 μl of serum and 450 μl of the diluent solution were used for each sample. In addition, the same test was conducted without using a silver chloride pipe. FIG. 9 shows the test results. In FIG. 9, curve i indicates the case wherein a silver chloride pipe was used, and curve j indicates the case wherein no silver chloride pipe was used. As is apparent from FIG. 9, when a silver chloride pipe is used, although electrode sensitivity tends to decrease slightly, practical sensitivity was maintained after 25,000 samples were measured.

TEST EXAMPLE 6

In this test, the apparatus of FIG. 3 was used, and a chloride ion concentration in serum was continuously measured over time. Normal serum containing about $10^{-4}$M of bromide ions and about $10^{-1}$M of chloride ions was used, with a tris-borate buffer solution containing $10/9 \times 7.5 \times 10^{-5}$M of silver ions used as a diluent solution. (This concentration is sufficient to provide silver ions corresponding to a bromide ion concentration in 1/10 diluted serum and to provide silver chloride of a saturate concentration in 1/10 diluted serum. The bromide ions bond with the dissolved silver ions to form silver bromide and is precipitated, thus improving the precision of measurement of chloride ion concentration. Since silver chloride of a saturated concentration is present in the diluted serum, elution of silver chloride from a silver/silver chloride electrode can be prevented.)

100 μl of serum and 900 μl of the diluent solution were used for each sample. As a result, a coefficient of variation cv during chloride ion concentration measurement could be kept below 0.5%, and continuous measurement could be continued for 6 months or longer. When no silver ions were used, the variation coefficient cv exceeded 2%, and working life of the electrode was 3 weeks.

According to the present invention as described above, halogen ions in a solution can be measured with short response time and high precision over a long period of time.

What is claimed is:

1. A method for measuring a halogen ion concentration in a solution, comprising the steps of:
    bringing halogen ion-selective detection means comprising a silver/silver halide electrode, and a reference electrode into a solution whose halogen ion concentration is to be measured; and
    measuring an electromotive force of said halogen ion-selective detection means corresponding to the halogen ion concentration in the solution with the presence of silver ions predissolved in the solution.

2. A method according to claim 1, wherein silver ions are supplied from a water soluble silver compound.

3. A method according to claim 2, wherein the silver compound is a material selected from the group consisting of silver halides and silver nitrate.

4. A method according to claim 3, wherein a silver ion concentration in the solution is lower than a saturated solution of the silver compound.

5. A method according to claim 1, wherein the solution is blood, the blood being diluted with a diluent solution containing silver ions, and the diluted blood is subjected to the step of measuring the electromotive force.

6. A method according to claim 1, wherein silver ions are dissolved in the solution by passing the solution through a flow path having an inner surface comprising a silver halide, and the solution which has passed through the flow path is subjected to the step of measuring the electromotive force.

7. A method according to claim 1, further comprising the step of washing the silver/silver halide electrode with a washing solution after the electromotive force is measured.

8. A method according to claim 7, wherein the washing solution contains dissolved silver ions.

9. A method according to claim 1, further comprising the step of calibrating the silver/silver halide electrode using a calibration solution after the electromotive force is measured.

10. A method according to claim 9, wherein the calibration solution contains dissolved silver ions.

11. An apparatus for measuring a halogen ion concentration in a solution, comprising:
    an ion-selective electrode unit including a halogen ion-selective electrode comprising a silver/silver halide electrode;
    a cell, having a flow path for the solution, for supporting said ion-selective electrode unit so as to expose it into said flow path;
    means for introducing the solution into said flow path of said cell;
    means for dissolving silver ions in the solution;
    potential measurement means for measuring a potential of said ion-selective electrode unit when the solution in which the silver ions are dissolved is introduced into said flow path; and
    means for calculating an ion concentration in the solution based on the potential measured by said potential measurement means.

12. An apparatus according to claim 11, further comprising means for introducing a washing solution, in which silver ions are dissolved, into said flow path of said cell after the ion concentration in the solution is measured.

13. An apparatus according to claim 11, further comprising means for introducing a calibration solution, in which silver ions are dissolved, into said flow path of said cell after a predetermined number of ion measurement operations are completed.

14. An apparatus according to claim 11, wherein said silver ion dissolving means comprises means for introducing a diluent solution in which silver ions are dissolved into the solution.

15. An apparatus according to claim 11, wherein said silver ion dissolving means is pipe means provided between said solution introducing means and said cell, and has an inner surface comprising a silver halide.

* * * * *